US00PP29986P3

(12) United States Plant Patent
Brazelton et al.

(10) Patent No.: US PP29,986 P3
(45) Date of Patent: Dec. 18, 2018

(54) BLUEBERRY PLANT NAMED 'FF03-015'

(50) Latin Name: *Vaccinium corymbosum*
Varietal Denomination: FF03-015

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Eugene, OR (US); Antonio A. Alamo Bermudo, Seville (ES); Paul Lyrene, Micanopy, FL (US)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 0 days.

(21) Appl. No.: 15/731,010

(22) Filed: Apr. 6, 2017

(65) Prior Publication Data

US 2017/0295681 P1 Oct. 12, 2017

Related U.S. Application Data

(60) Provisional application No. 62/390,716, filed on Apr. 6, 2016.

(51) Int. Cl.
*A01H 5/08* (2018.01)

(52) U.S. Cl.
USPC ..... Plt./157
CPC ..... *A01H 5/08* (2013.01)

(58) Field of Classification Search
USPC ..... Plt./157
See application file for complete search history.

*Primary Examiner* — Susan McCormick Ewoldt
(74) *Attorney, Agent, or Firm* — Hahn Loeser & Parks, LLP

(57) ABSTRACT

The new blueberry plant variety 'FF03-015' is provided. 'FF03-015' is a commercial variety intended for the hand harvest, fresh market. The variety is produced from a cross of 'FL95-52' and 'Sunshine Blue', and can be distinguished by its outstanding features. The variety has good vigor, ripens very early and produces excellent yields of large berries with good flavor.

8 Drawing Sheets

Latin name of the genus and species:
Genus—*Vaccinium.*
Species—*corymbosum.*
Variety denomination: The new blueberry plant claimed is of the variety denominated 'FF03-015'.

STATEMENT REGARDING FEDERALLY-SPONSORED RESEARCH AND DEVELOPMENT

None.

BACKGROUND OF THE INVENTION

The present invention relates to the discovery of a new and distinct cultivar of southern highbush blueberry (*Vaccinium corymbosum* L. hybrid) plant, referred to as 'FF03-015', as herein described and illustrated. The cross that produced 'FF03-015' was made in Florida, and seeds were subsequently sent to Oregon for germination and evaluation of the resulting seedlings. The new blueberry plant variety 'FF03-015' was selected in Lowell, Oreg. in 2010 because its fruit ripened early and had good flavor. 'FF03-015' is a commercial variety intended for the hand harvest fresh market. The variety has good vigor, ripens very early and produces excellent yields of large berries with good flavor. After being selected as a seedling in Oregon, 'FF03-015' was trialed in California, USA; Colima, Mexico; and Huelva, Spain. When grown under protected tunnels in an evergreen production system in Spain, 'FF03-015' produced excellent yields of large fruit for such an early ripening variety.

SUMMARY OF THE INVENTION

Pedigree and History: The new blueberry plant originated from a cross of 'FL95-52' (female parent, unpatented) by 'Sunshine Blue' (pollen parent, unpatented). The cross that produced 'FF03-015' was made in Gainesville, Fla., USA in 2000.

The new *Vaccinium* hybrid cultivar is a selection resulting from seedlings produced in a controlled breeding program of *Vaccinium* at Lowell, Oreg., USA in 2010 from the controlled pollination of seed parent 'FL95-52' (unpatented) and pollen parent 'Sunshine Blue' (unpatented).

Asexual reproduction of the new cultivar by cutting propagation since the 2010 at Lowell, Oreg., USA has demonstrated that the new cultivar reproduces true to type with all the characteristics, as herein described, firmly fixed and retained through successive generations of such asexual propagation.

The new cultivar was selected as a single plant within a population of plants resulting from this controlled pollination of *Vaccinium* hybrids in the year 2010 in a commercial field planting environment at Lowell, Oreg. Selection criteria were a combination of good vigor, very early ripening and excellent yields of large berries with good flavor. The selection was subsequently evaluated for 5 years at Lowell, Oreg. USA.

The following characteristics of the new cultivar have been repeatedly observed and can be used to distinguish 'FF03-015' as a new and distinct cultivar of *Vaccinium* hybrid plant:

1. Growth habit—Upright, round
2. Timing of beginning of flowering—Flowering throughout the year, from end of February to end of May.

3. Timing of fruit ripening—Start at the middle of April in Lowell, Oreg.
4. Plant growth vigor—Vigorous.
5. Berry color—Ripe berry color from Pantone colors Dapple Gray 16-3907 to Crown Blue 19-3926.
6. Berry firmness—Low.
7. Picking scar—Small with an average of 1.4 mm in diameter.
8. Leaf width—Average of 24.78 mm.
9. Berry size—Medium-small with a diameter average of 14.79 mm.
10. Berry sweetness—Moderate.

The female parent 'FL95-52' has not been evaluated side by side with 'FF03-015' in the same environment. However, the new variety differs from the unpatented male parent 'Sunshine Blue' in that 'FF03-015' is a tall upright bush, that produces very early light blue fruit, while 'Sunshine Blue' is a semi-dwarf round bush, with midseason, medium dark colored fruit. The new blueberry plant variety 'FF03-015' has maintained its distinguishing characteristics throughout successive asexual propagations. The variety has been repeatedly asexually reproduced through softwood cuttings in Lowell, Oreg., and the clones are phenotypically identical to the original plant.

BRIEF DESCRIPTION OF THE DRAWINGS

The accompanying photographic illustration shows typical specimens in full color of the foliage and fruit of the new variety 'FF03-015'. The colors are as nearly true as is reasonably possible in a color representation of this type.

Figure 1:
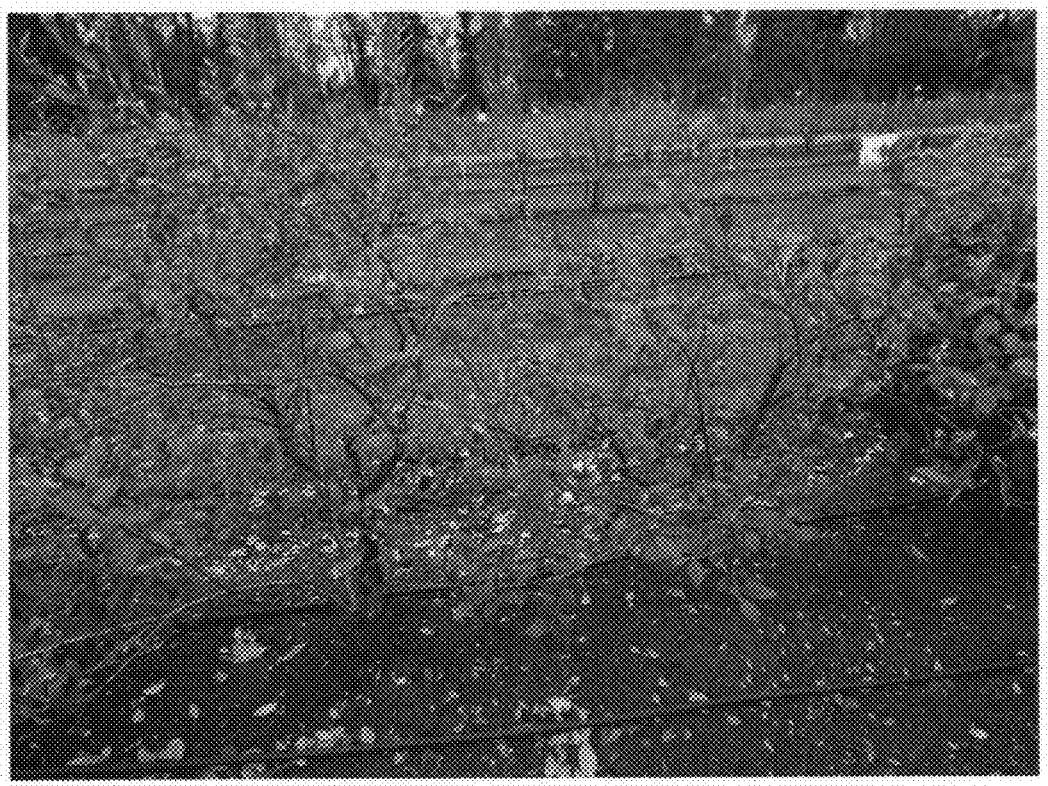
FIG. 1 is a photograph of the whole plant of the new variety 'FF03-015'.
Figure 2:
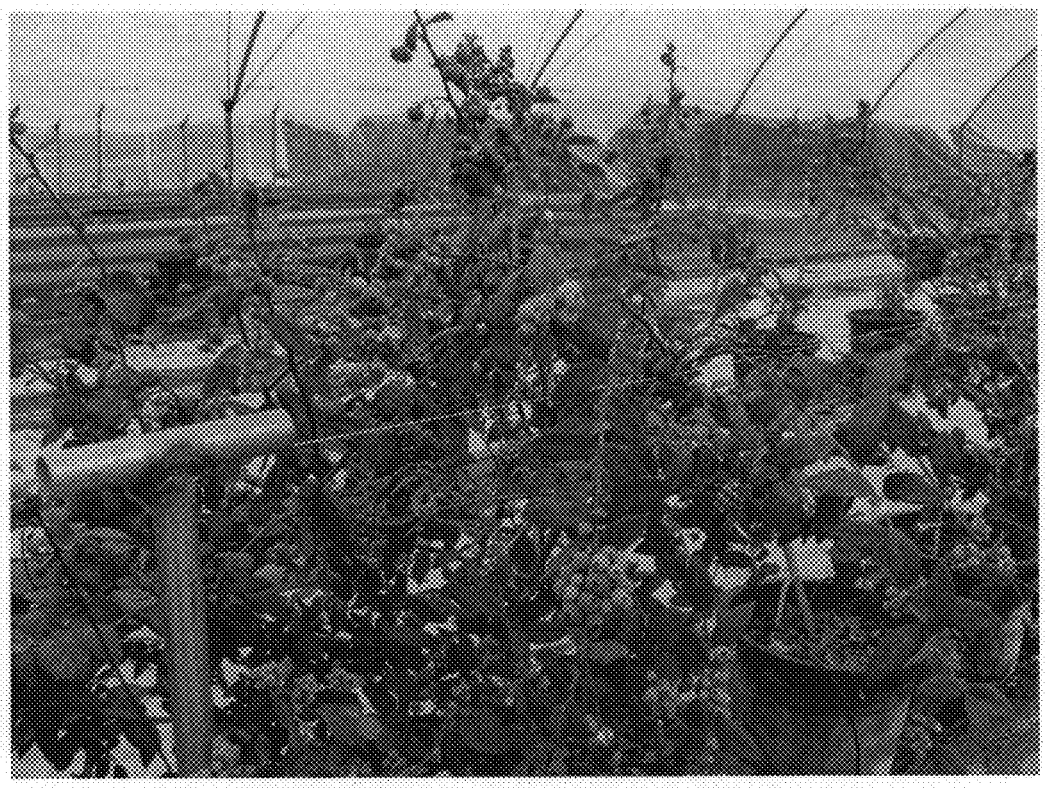
FIG. 2 is a photograph of the whole plant with fruit of the new variety 'FF03-015'.
Figure 3:
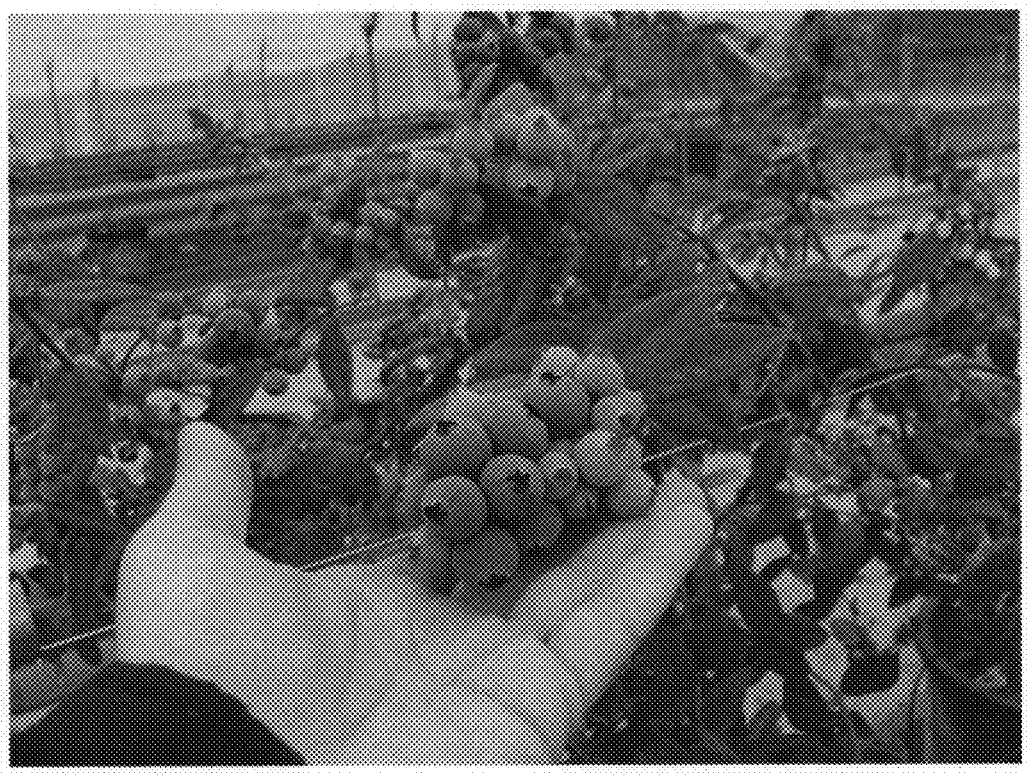
FIG. 3 is a photograph of the fruit of the new variety 'FF03-015'.
Figure 4:
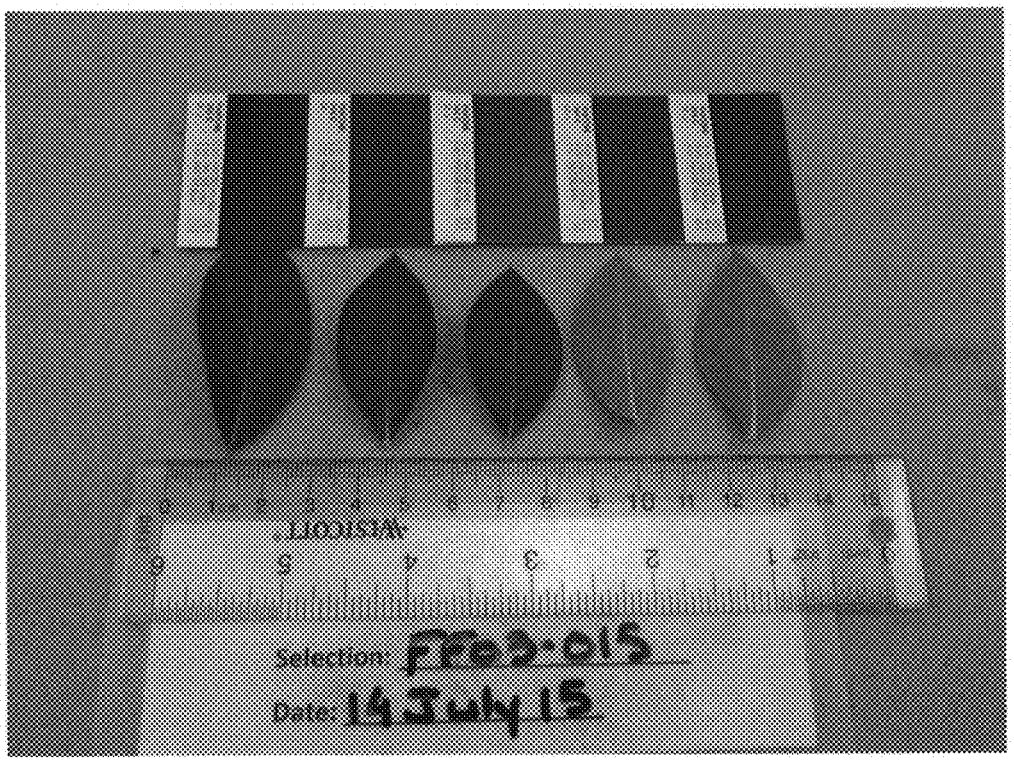
FIG. 4 is a photograph of the leaves of the new variety 'FF03-015'.
Figure 5:
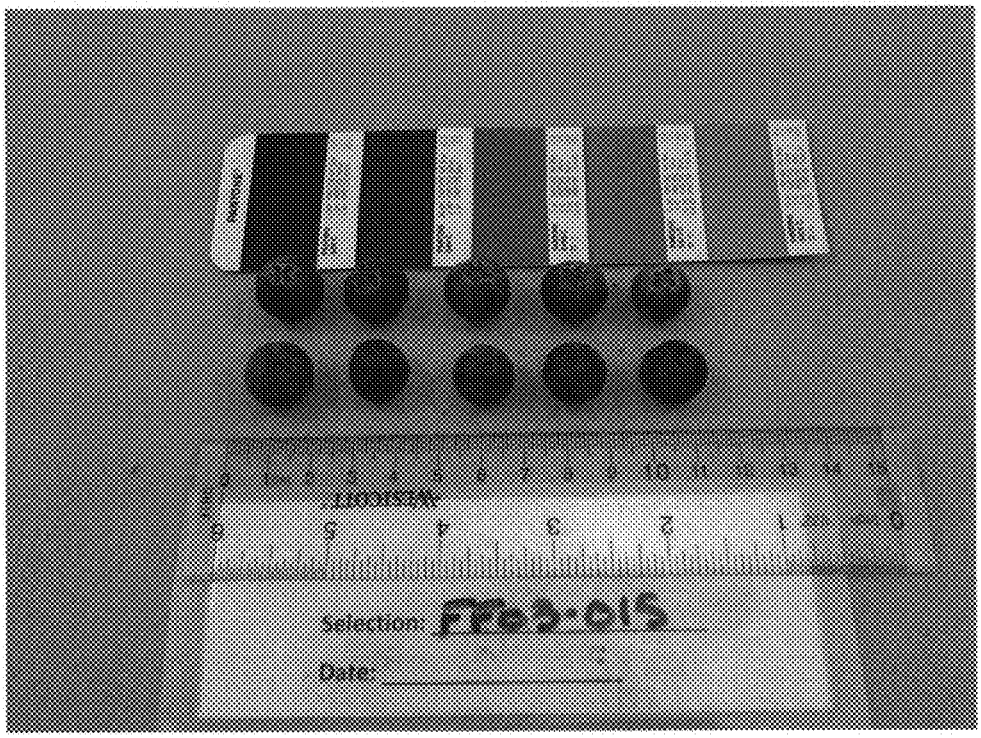
FIG. 5 is a photograph of the fruit of the new variety 'FF03-015'.
Figure 6:
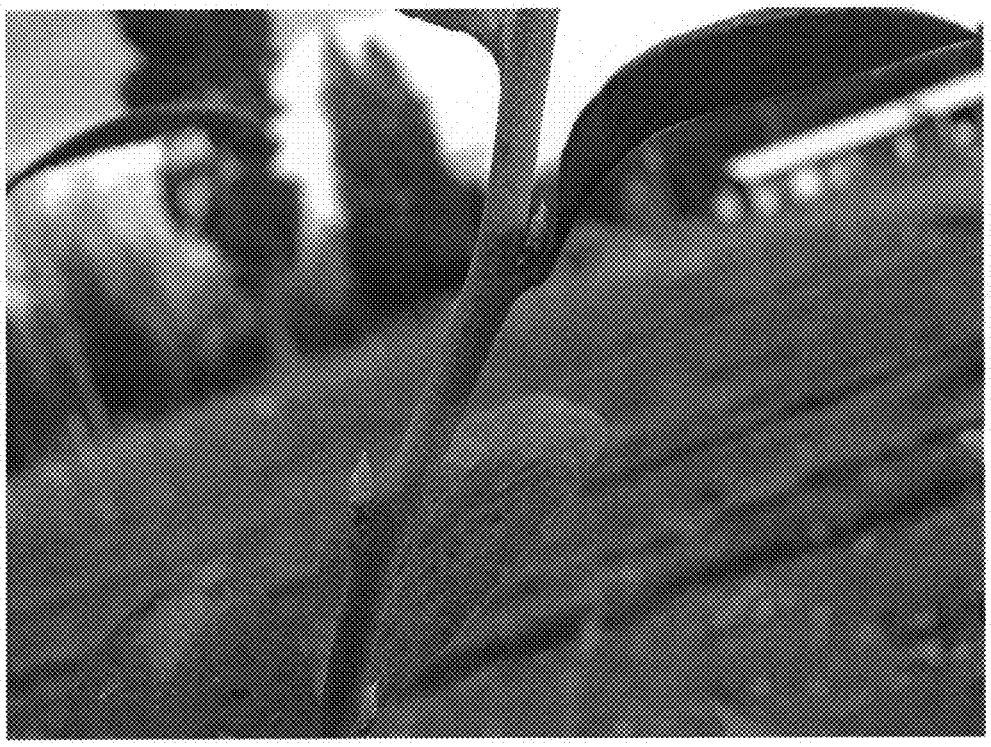
FIG. 6 is a photograph of stem of the new variety 'FF03-015'.
Figure 7:
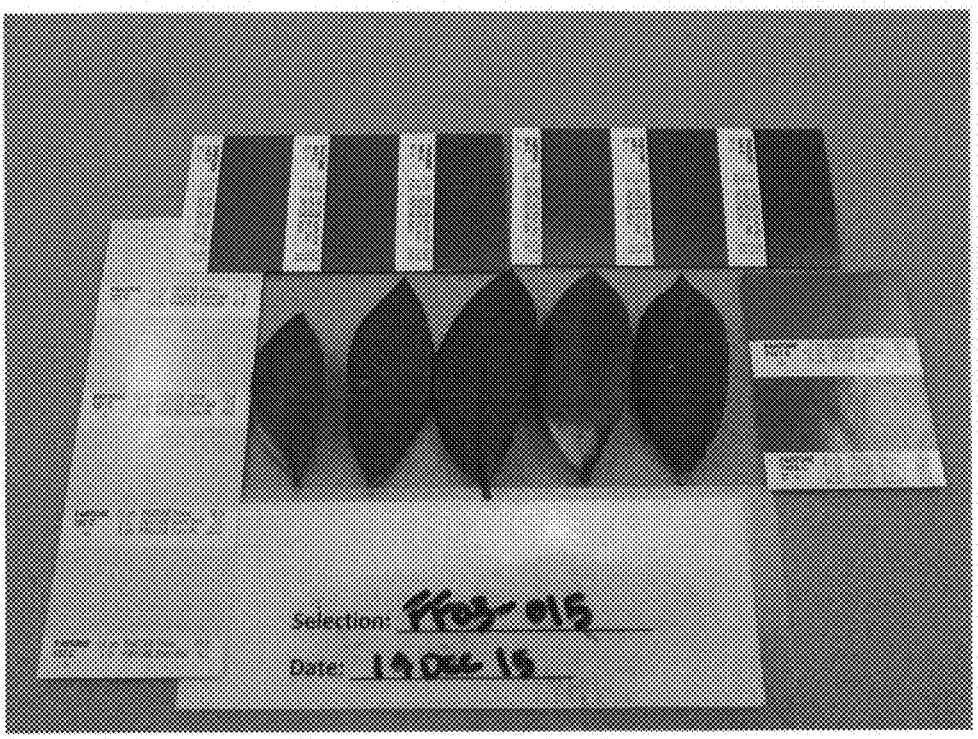
FIG. 7 is a photograph of the leaves of the new variety 'FF03-015'.
Figure 8:
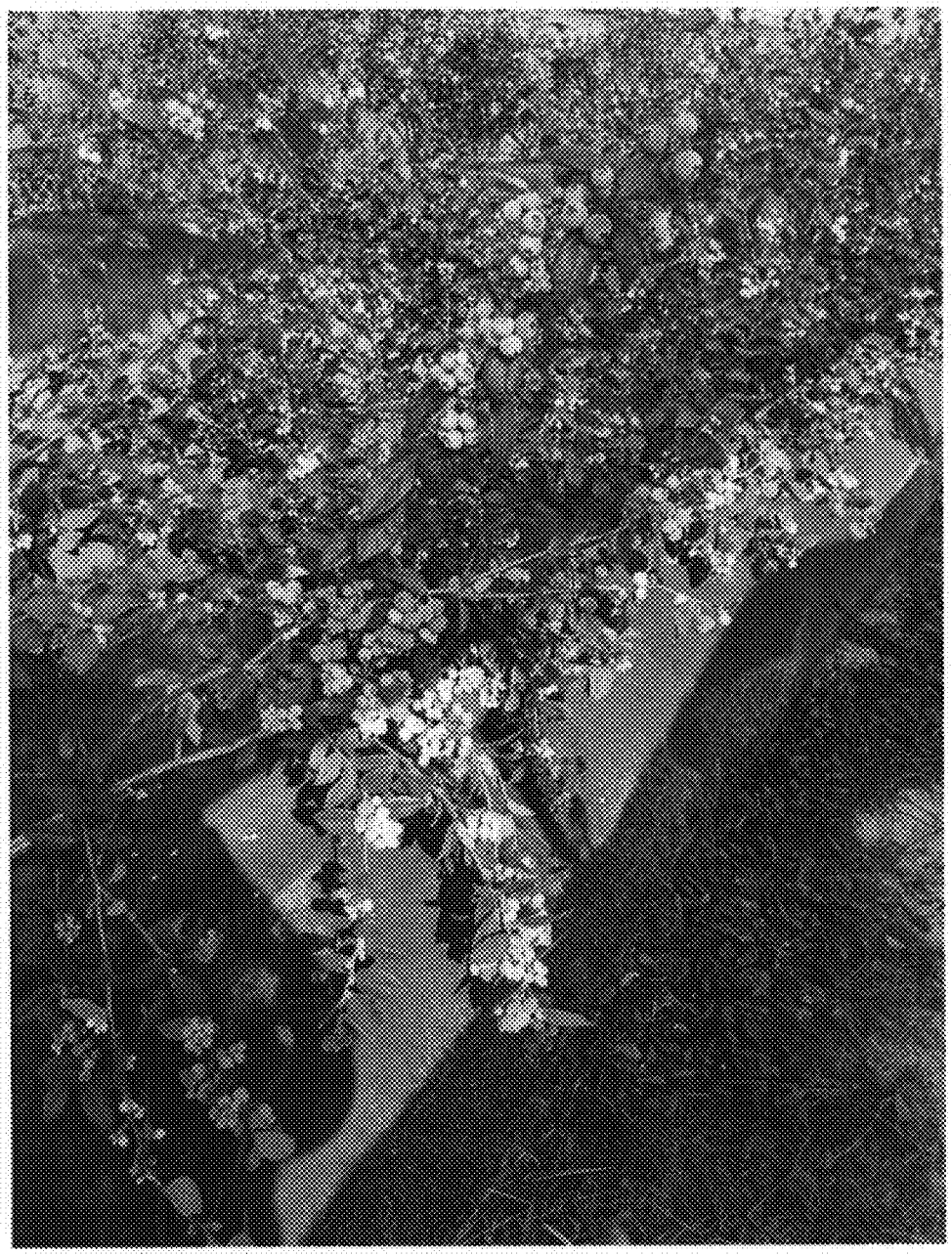
FIG. 8 is a photograph of the whole plant with fruit of the new variety 'FF03-015'.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'FF03-015'. The data which defines these characteristics was collected from asexual reproductions of the original selection. Dimensions, sizes, colors, and other characteristics are approximations and averages set forth as accurately as possible. The plant history was taken on plants approximately 5 years of age, and the descriptions relate to plants grown in the field in Lowell, Oreg. Descriptions of fruit characteristics were made on fruit grown in Lowell, Oreg. Color designations are from Pantone color code source. Color designations are from The Pantone Book of Color: Over 1000 Color Standards: Color Basics and Guidelines for Design, Fashion, Furnishings . . . and More (by Leatrice Eiseman and Lawrence Herbert, Harry N. Abrams, Inc., Publishers, New York, 1990).

Classification:

a. *Family.*—Ericaceae.
b. *Genus.*—*Vaccinium.*
c. *Species.*—*corymbosum.*
d. *Common name.*—Blueberry.

Parentage: Female Parent — 'FL95-52' (unpatented). Male Parent — 'Sunshine Blue' (unpatented).

Market class: Hand harvest, fresh market.

PLANT

General:

a. *Parentage.*—'FL95-52' x 'Sunshine Blue'.
b. *Plant height.*—Average of 1.0 m.
c. *Plant width.*—Average of 1.3 m.
d. *Growth habit.*—Round.
e. *Growth type.*—Medium-vigorous.
f. *Productivity.*—High.
g. *Cold hardiness.*—Null-low.
h. *Cold tolerance.*—Low.
i. *Chilling requirement.*—Low, less than 600 hours.
j. *Tolerance to disease.*—Good.
k. *Leafing.*—Heavy leafing.
l. *Twigginess.*—Low.

STEM

General:

a. *Suckering tendency.*—Low.
b. *Mature cane color.*—Pantone colors Moonlight 15-1309, Pecan Brown 17-1430, Stucco 16-1412, Sand 15-1225, Raw Umber 17-1422.
c. *Mature cane length.*—Average of 27 cm.
d. *Mature cane width.*—Average of 16 mm.
e. *Bark texture.*—Rough.
f. *Fall color on new shoots.*—Pantone colors Holly Berry 17-1633, Green Oasis 15-0538, Faded Rose 18-1629, Mineral Red 17-1537.
g. *Surface texture of new wood.*—Smooth.
h. *Internode length on strong, new shoots.*—Average 19.1 mm.
i. *Fruiting wood.*—average of 16 cm in length.

FOLIAGE

General:

a. *Time of beginning of leaf bud burst.*—In Lowell, Oreg. late February to early March.
b. *Leaf color* (*top side*).—New leaf colors: Peridot 17-0336, Chive 19-0323, Crushed Berry 18-1418, Plum Wine 18-1411, Herbal Garden 15-0336.
c. *Leaf color* (*under side*).—Pantone color Water Cress 17-0220.
d. *Leaf arrangement.*—Alternate.
e. *Leaf shape.*—Elliptic.
f. *Leaf margins.*—Entire to crenulate.
g. *Undulation of margin.*—Entire.
h. *Leaf venation.*—Pinnate.
i. *Leaf apices.*—Acuminate.
j. *Leaf bases.*—Acute.
k. *Leaf length.*—Average 50.64 mm.
l. *Leaf width.*—Average 24.78 mm.
m. *Leaf length/width ratio.*—Medium.

n. *Leaf nectarines*.—Absent.
o. *Pubescence of upper side*.—Absent.
p. *Pubescence of lower side*.—Absent.
q. *Cross sectional profile*.—Plane.
r. *Longitudinal profile*.—Plane.
s. *Attitude*.—Ascending.

Petioles:
a. *Length*.—Average 1.03 mm.
b. *Width*.—Average 0.97 mm.
c. *Color*.—Pantone color Green Banana 14-0434.

FLOWERS

General:
a. *Time of beginning of flowering*.—Flowered throughout the year, from end of February to end of May.
b. *Time of* 50% *anthesis*.—In Lowell, Oreg. late March.
c. *Flower shape*.—Urceolate to cylindrical.
d. *Flower bud density*.—Medium.
e. *Flower fragrance*.—Mild, sweet.

Corolla:
a. *Color*.—Pantone color Snow White 11-0602.
b. *Length*.—Average 8.2 mm.
c. *Width*.—Average 7.29 mm.
d. *Aperture width*.—Average 3.99 mm.
e. *Anthocyanin coloration of corolla*.—Low.
f. *Corolla ridges*.—Present.
g. *Protrusion of stigma*.—Average 0.14 mm below lip of corolla.

Inflorescence:
a. *Length*.—Average 2.26 cm.
b. *Diameter*.—Average 2.33 cm.
c. *Length of peduncle*.—Average 12.04 mm.
d. *Surface texture of peduncle*.—Smooth.
e. *Color of peduncle*.—Pantone colors Herbal Garden 15-0336 to Green Banana 14-0434 with some Red Earth 18-1444 and Redwood 18-1443.
f. *Length of pedicel*.—Average 3.78 mm.
g. *Surface texture of pedicel*.—Smooth.
h. *Color of pedicel*.—Pantone colors Mellow Green 12-0426 and small amount of Crushed Berry 18-1418 on some.
i. *Number of flowers per cluster*.—Average 6 flowers per cluster.
j. *Flower cluster density*.—Moderate to high.

Calyx (with sepals):
a. *Diameter*.—Average 4.14 mm.
b. *Color* (*sepals*).—Pantone colors Lettuce Green 13-0324 to Herbal Garden 15-0336.

Stamen:
a. *Length*.—Average 7.08 mm.
b. *Number per flower*.—10.
c. *Filament color*.—Pantone color Celery Green 13-0532.
d. *Style*.—Length — Average 7.98 mm.
e. *Color*.—Golden Ochre 16-1346.

Pistil:
a. *Length*.—Average 10.47 mm.
b. *Ovary color* (*exterior*).—Pantone colors Spinach Green 16-0439 to Grasshopper 18-0332 with small amount of Crushed Berry 18-1418 on some.

Anther:
a. *Length*.—Average 4.83 mm.
b. *Number*.—2.
c. *Color*.—Pantone colors Baked Clay 18-1441 to Raw Sienna 17-1436.

Pollen:
a. *Abundance*.—Moderate.
b. *Color*.—Pantone color Pale Banana 12-0824.
c. *Self-compatibility*.—Good.

FRUIT

General:
a. *Time of fruit ripening*.—Start at the middle of April in Lowell, Oreg.
b. *Time of* 50% *maturity*.—Middle of June.
c. *Fruit development period*.—63 days.
d. *Cluster density*.—Average of 5 berries per cluster.
e. *Unripe fruit color*.—Pantone colors Celery Green 13-0532, Holly Berry 17-1633, Maroon 18-1619.
f. *Ripe berry color*.—Pantone colors Dapple Gray 16-3907 to Crown Blue 19-3926.
g. *Berry surface wax abundance*.—Moderate wax that rubs easily.
h. *Berry flesh color*.—Pantone colors Pastel Yellow 11-0616 to Antique white 11-0105 to Vanilla 12-0712.
i. *Berry weight*.—Average 1.74 g.
j. *Berry height from calyx to scar*.—Average 13.06 mm.
k. *Berry diameter*.—Average 14.79 mm.
l. *Berry shape*.—Variable. Round, with some slightly oblate and others slightly spheroid.
m. *Fruit stem scar*.—Average 1.4 mm in diameter.
n. *Sweetness when ripe*.—Moderate.
o. *Firmness when ripe*.—Low.
p. *Acidity when ripe*.—Moderate.
q. *Storage quality*.—Good.
r. *Suitability for mechanical harvesting*.—Low.
s. *Self-fruitfulness*.—Good.
t. *Uses*.—Fresh Hand harvest.

SEED

General:
a. *Seed abundance in fruit*.—Average 19 seeds per berry.
b. *Seed color*.—Pantone color Aztec 18-1130.
c. *Seed dry weight*.—0.035 mg per 100 seeds.
d. *Seed length*.—Average 1.62 mm.

COMPARISON BETWEEN PARENTAL AND COMMERCIAL CULTIVARS

The new variety 'FF03-015' is different from 'FF04-014' (U.S. Plant Pat. No. 27,623 P3), another evergreen cultivar in that 'FF03-015' present an upright growth habit vs 'FF04-014' that is more round shape. 'FF03-015' is also early producer of lighter or waxier, smaller berries than 'FF04-014'.

TABLE 1

| Name of variety: | Characteristics: | Differences: |
|---|---|---|
| 'FF04-014' | Growth habit | Upright |
| 'FF04-014' | Season | Earlier |
| 'FF04-014' | Fruit color | Lighter |
| 'FF04-014' | Fruit size | Smaller |
| 'Star' (U.S. Plant Pat. No. 10,675) | Leaf retention | Evergreen |

The invention claimed is:

1. A new and distinct variety of blueberry plant named 'FF03-015', substantially as illustrated and described herein.

* * * * *